(12) United States Patent
Kim et al.

(10) Patent No.: US 7,189,560 B2
(45) Date of Patent: Mar. 13, 2007

(54) METHODS AND APPARATUSES OF SEPARATING CELLS USING MAGNETS AND DROPLET TYPE CELL SUSPENSION

(75) Inventors: Young-Ho Kim, Seoul (KR); Byeong-Kwon Ju, Seoul (KR); Seok Yun, Seoul (KR); Yu-Ri Kang, Paju-si (KR); Kyeong-Kap Paek, Seoul (KR); Jin-Woo Lee, Seoul (KR); Byung Kyu Kim, Seoul (KR); Jong Oh Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/878,357

(22) Filed: Jun. 28, 2004

(65) Prior Publication Data

US 2005/0227349 A1     Oct. 13, 2005

(30) Foreign Application Priority Data

Apr. 13, 2004   (KR) ...................... 10-2004-0025421

(51) Int. Cl.
*C12M 1/42* (2006.01)
(52) U.S. Cl. ............................... 435/308.1; 435/287.2; 435/288.5; 422/73; 436/63; 436/526
(58) Field of Classification Search ............. 435/308.1; 436/526, 63
See application file for complete search history.

(56) References Cited

U.S. PATENT DOCUMENTS 5,646,001 A * 7/1997 Terstappen et al. ........ 435/7.21

OTHER PUBLICATIONS

Rong Rong et al., "A Functional Magnetic Bead/Biocell Sorter Using Fully Integrated Magnetic Micro/Nano Tips," IEEE the 16th Annual International Conference on MEMS, Jan. 19-23, 2003; pp. 530-533, 03CH37426.
Tao Deng et al., "Fabrication of Magnetic Microfiltration Systems Using Soft Lithography," Applied Physics Letters, vol. 80, No. 3; Jan. 21, 2002; pp. 461-463.
Michael Berger et al., "Design of a Microfabricated Magnetic Cell Separator," Electrophoresis, vol. 22, No. 16, Oct. 2001; pp. 3883-3892.

* cited by examiner

*Primary Examiner*—William H. Beisner
(74) *Attorney, Agent, or Firm*—Armstrong, Kratz, Quintos, Hanson & Brooks, LLP

(57) ABSTRACT

Disclosed are methods and apparatuses for separating cells using magnets and droplet type cell suspension according to the present invention, which may effectively separate cells by forming droplet type cell suspension with cell suspension sample containing cells to which magnetic beads are coupled and applying magnetic force to the droplet type cell suspension.

The apparatus of separating cells according to the present invention includes: a droplet type cell suspension forming part for forming a droplet type cell suspension under a lower part of the droplet type cell suspension forming part with cell suspension sample containing cells to which magnetic beads are coupled; a cell suspension inlet for supplying the droplet type cell suspension forming part with the cell suspension sample; a magnet for applying magnetic force to the droplet type cell suspension; a cell buffer inlet for supplying the droplet type cell suspension with cell buffer; and a temperature maintaining part for maintaining a temperature of the droplet type cell suspension.

13 Claims, 3 Drawing Sheets

METHODS AND APPARATUSES OF SEPARATING CELLS USING MAGNETS AND DROPLET TYPE CELL SUSPENSION

CROSS-REFERENCE TO RELATED APPLICATION

The entire disclosure of Korean Patent Application No. 10-2004-0025421 filed on Apr. 13, 2004 including specification, claims, drawings and summary, is incorporated herein by reference in its entirety.

BACKGROUND OF THE INVENTION

1. Field of the Invention

The present invention relates to methods and apparatuses of separating cells, and more particularly to methods and apparatuses of separating cells using magnets and droplet type cell suspension, which may effectively separate cells by forming droplet type cell suspension with cell suspension sample containing cells to which magnetic beads are coupled and applying magnetic force to the droplet type cell suspension.

2. Description of the Related Art

Methods of separating cells in the related art are classified into two methods. Specifically, a first method is to separate cells using a tube type apparatus of separating using magnetic force and gravitation and a second method is to separate cells using sizes of cell transport channel and cells.

The first method occupies 70~80% of cell separation methods that are currently performed. The method is performed in a manner that many metal balls of ferrite are provided in the tube type cell separation apparatus and magnetic field is applied to the tube type cell separation apparatus while cell suspension is inputted into the tube type cell separation apparatus in a gravitational direction.

At this time, since cells to be separated are coupled to a magnetic bead by using antigen-antibody reaction, the cells tend to stick to a surrounding magnetic body. Accordingly, the metal balls made of paramagnetic ferrite become magnetized when the magnetic field is applied while cell suspension is inputted, so that the cells to which magnetic beads are coupled stick to the metal balls.

According to the first method, metal balls having a diameter of 50~100 μm are mostly used. However, since a size of a void between the metal balls is variable depending on the sizes of the metal balls, the size of the metal ball should be adjusted all the time so as to separate cells having various sizes.

Further, since the cells to be separated are in contact with the metal balls, an absorption tends to occur. In addition, when the cells lump, it is difficult for the cells to pass through the void between the metal balls, so that a sieve should be used before separating.

Second, according to the second method of separating cells using sizes of cell transport channel and cells to be separated, a channel through which cell suspension containing cells to be separated passes is formed and another channel adapted to a size of the cells to be separated is formed at an end of the channel, so that the cells to be separated moves only via the channel adapted to a size of the cells to be separated.

According to the second method, like the first method, a new channel should be formed depending on a size of cells to be separated. Further, when cells having a size smaller than that of cells to be separated are mixed, it is difficult to discriminate cells at a time.

BRIEF SUMMARY OF THE INVENTION

Accordingly, the present invention has been made to solve the above-mentioned problems occurring in the related art. The object of the present invention is to provide methods and apparatuses of separating cells that may effectively separate cells without adjusting the apparatus all the time depending on a size of cells to be separated.

In order to accomplish the objects, there is provided an apparatus of separating cells using magnets and droplet type cell suspension including: a droplet type cell suspension forming part for forming a droplet type cell suspension under a lower part of the droplet type cell suspension forming part with cell suspension sample containing cells to which magnetic beads are coupled; a cell suspension inlet for supplying the droplet type cell suspension forming part with the cell suspension sample; a magnet for applying magnetic force to the droplet type cell suspension; a cell buffer inlet for supplying the droplet type cell suspension with cell buffer; and a temperature maintaining part for maintaining a temperature of the droplet type cell suspension.

Preferably, the apparatus further includes: an outlet for discharging cell buffer and cell suspension sample left after the cells to which magnetic beads are coupled are separated; and a droplet type cell suspension protecting part, connected to the outlet and spaced apart from the droplet type cell suspension forming part by a predetermined distance, for protecting the droplet type cell suspension.

Preferably, the droplet type cell suspension forming part may regulate a size of droplet type cell suspension to be formed.

Preferably, the magnet may apply attraction force to the cells to which the magnetic beads are coupled in the droplet type cell suspension.

Preferably, the magnet is not fixedly connected to the droplet type cell suspension forming part and is able to be easily separated from the droplet type cell suspension forming part.

Preferably, the temperature maintaining part may maintain temperatures of the droplet type cell suspension and the droplet type cell suspension protecting part.

Preferably, the temperature maintaining part may perform a cooling and a keeping warm simultaneously.

Preferably, the temperature maintaining part may be implemented by a peltier element.

Preferably, the droplet type cell suspension protecting part may prevent the droplet type cell suspension from evaporating.

Preferably, the droplet type cell suspension may be formed under a lower part of the droplet type cell suspension forming part.

Preferably, the cell buffer inlet may regulate vertical location of the cell buffer inlet itself.

Preferably, a region, where the droplet type cell suspension is to be formed, of the droplet type cell suspension forming part may have hydrophilic property and the other region of the droplet type cell suspension forming part may have hydrophobic property.

In order to accomplish the above objects, there is provided a method of separating cells using magnets and droplet type cell suspension including: forming a droplet type cell suspension with cell suspension sample containing cells to which magnetic beads are coupled; applying magnetic force to the droplet type cell suspension; supplying the droplet type cell suspension with cell buffer; and separating the cells to which magnetic beads are coupled from the droplet type cell suspension.

Preferably, said applying magnetic force to the droplet type cell suspension may move the cells, to which magnetic beads are coupled, in the droplet type cell suspension in a certain direction.

Preferably, said supplying the droplet type cell suspension with cell buffer may be for moving the cell suspension sample, left after the cells to which magnetic beads are coupled are separated, in a gravitational direction.

Preferably, said separating the cells to which magnetic beads are coupled from the droplet type cell suspension is to separate the cells to which magnetic beads are coupled after the applied magnetic force is removed.

Preferably, said separating the cells to which magnetic beads are coupled from the droplet type cell suspension is to separate the cells to which magnetic beads are coupled and, then, to remove the applied magnetic force.

Preferably, temperatures of the droplet type cell suspension and the cells to which magnetic beads are coupled are maintained at a predetermined temperature.

In order to achieve the above objects, there is provided another apparatus of separating cells using magnets and droplet type cell suspension, including: a droplet type cell suspension forming part for forming a droplet type cell suspension under a lower part of the droplet type cell suspension forming part with cell suspension sample containing cells to which magnetic beads are coupled; a cell suspension inlet for supplying the droplet type cell suspension forming part with the cell suspension sample; a magnet for applying magnetic force to the droplet type cell suspension; a cell buffer inlet for supplying the droplet type cell suspension with cell buffer and regulating vertical location of the cell buffer inlet itself; and a droplet type cell suspension protecting part, connected to the outlet and spaced apart from the droplet type cell suspension forming part by a predetermined distance, for protecting the droplet type cell suspension.

Preferably, the apparatus may further include an outlet for discharging cell buffer and cell suspension sample left after the cells to which magnetic beads are coupled are separated.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Hereinafter, the cells to which magnetic beads are coupled and to be separated from droplet type cell suspension will be referred to as "specific cells."

Figure 1:
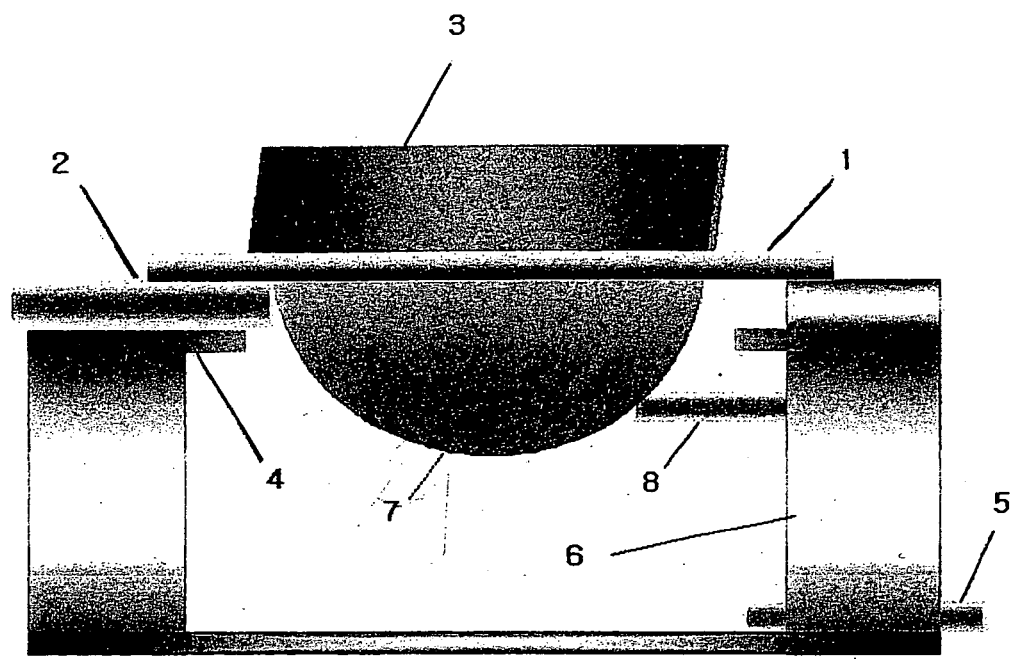
FIG. 1 illustrates an apparatus of separating cells using magnets and droplet type cell suspension according to a preferred embodiment of the present invention.

FIG. 1 illustrates an apparatus of separating cells using magnets and droplet type cell suspension according to a preferred embodiment of the present invention.

Referring to FIG. 1, an apparatus of separating cells using magnets and droplet type cell suspension according to a preferred embodiment of the present invention includes a droplet type cell suspension forming part 1 for forming a droplet type cell suspension under a lower part of the droplet type cell suspension forming part with cell suspension sample containing specific cells; a cell suspension inlet 2 for supplying the droplet type cell suspension forming part with the cell suspension sample; a magnet 3 for applying magnetic force to the droplet type cell suspension; a cell buffer inlet 8 for supplying the droplet type cell suspension with cell buffer; a temperature maintaining part 4 for maintaining a temperature of the droplet type cell suspension; an outlet 5 for discharging cell buffer and cell suspension sample left after the specific cells are separated from the droplet type cell suspension; and a droplet type cell suspension protecting part 6, connected to the outlet and spaced apart from the droplet type cell suspension forming part 1 by a predetermined distance, for protecting the droplet type cell suspension.

According to the apparatus of separating cells, a droplet type cell suspension is formed under a lower part of the droplet type cell suspension forming part 1, as cell suspension sample containing specific cells is injected through the cell suspension inlet 2 to the droplet type cell suspension forming part 1. Further, the magnet 3 is positioned on an upper part of the droplet type cell suspension forming part 1.

The magnet 3 may be a permanent magnet, a magnetic body able to be magnetized by applying an exterior magnetic field or an electromagnet and be differently embodied as required.

The droplet type cell suspension forming part 1 has a flat plate shape, and a surface where the droplet type cell suspension is formed is coated with hydrophilic and hydrophobic materials, so that a size of the droplet type cell suspension can be regulated. For example, when it is desired to form droplet type cell suspension having a diameter of 7 mm or less, an inner part of a region, having a diameter of 7 mm, where the droplet type cell suspension is to be formed is coated with the hydrophilic material and an outer part of the region is coated with the hydrophobic material. Therefore, the hydrophobic material functions as a film or a boundary for preventing droplet type cell suspension from forming on the outer part, so that droplet type cell suspension having a diameter of 7 mm or less can be formed.

The cell suspension inlet 2 supplies the droplet type cell suspension forming part 1 with cell suspension sample containing the specific cells to form droplet type cell suspension under a lower part of the droplet type cell suspension forming part 1. On the other hand, the cell buffer inlet 8 supplies the droplet type cell suspension formed under the lower part of the droplet type cell suspension forming part 1 with only cell buffer to drop the cell suspension sample left after the specific cells are separated and may regulate vertical location of itself to prevent the specific cells already separated and the other cells etc. in the droplet type cell suspension from congregating.

Meanwhile, the temperature maintaining part 4 is positioned under a lower part of the cell suspension inlet 2, has a flat plate shape like the droplet type cell suspension forming part 1 and prevents temperature of the formed droplet type cell suspension from increasing. Further, the temperature maintaining part 4 maintains temperature of droplet type cell suspension protecting part 6. Like this, the temperature maintaining part 4 prevents temperature of the formed droplet type cell suspension from increasing and temperature of the droplet type cell suspension protecting part 6 from decreasing, at the same time. Therefore, the droplet type cell suspension protecting part 6 is protected from moisture, etc. that may occur in the droplet type cell suspension protecting part 6.

In order to perform the above functions, both sides of the temperature maintaining part 4 are made of peltier elements capable of cooling and keeping warm at the same time.

The droplet type cell suspension protecting part 6 functions as a chamber of the apparatus of separating cells according to the present invention, and are constructed to secure a space having a size of not deterring the droplet type cell suspension formation, so that the formed droplet type cell suspension is protected from an influence of the exterior.

Figure 2:
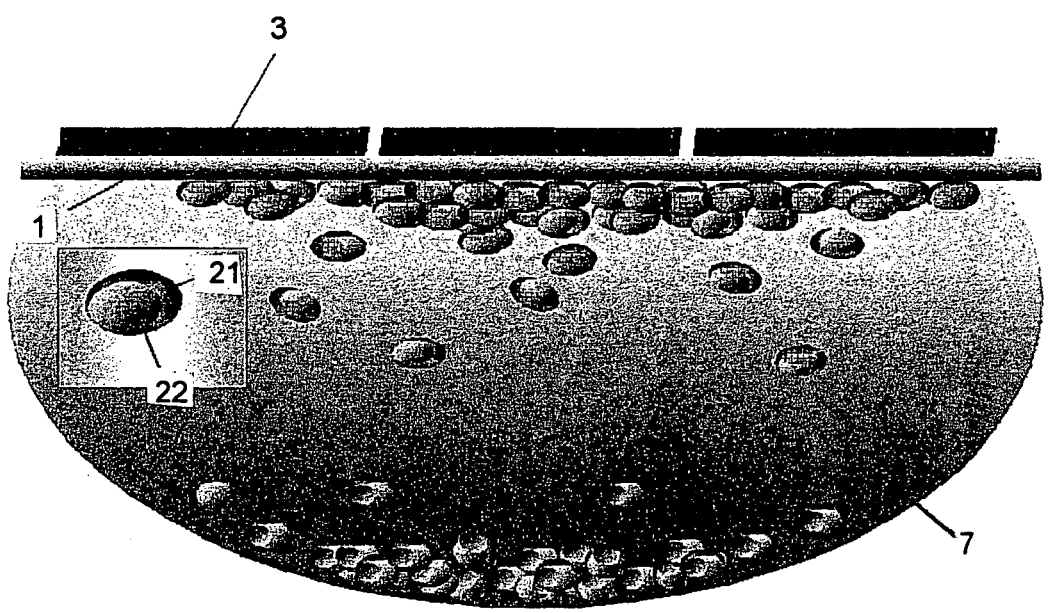
FIG. 2 illustrates an interior of the droplet type cell suspension shown in FIG. 1.

FIG. 2 illustrates an interior of the droplet type cell suspension shown in FIG. 1 and is provided to illustrate a basic principle of the method and apparatus of separating cells according to the present invention.

When the cell suspension sample containing the specific cells is supplied to the droplet type cell suspension forming part 1 via the cell suspension inlet 2, droplet type cell suspension 7 is formed under a lower part of the droplet type cell suspension forming part 1.

There are the specific cells 21, cell buffer and the other cells in the droplet type cell suspension 7, wherein the specific cells are cells to which magnetic beads are coupled by using antigen-antibody reaction.

Therefore, the specific cells 21 are moved in the droplet type cell suspension in a certain direction (e.g. in the opposite direction of gravitation) when the droplet type cell suspension is formed or after magnetic force is applied by the magnet 3, according to the embodied form of the magnet 3.

In other words, attraction force is applied to the specific cells 21, so that the specific cells are moved in the droplet type cell suspension towards the droplet type cell suspension forming part 1 and the other cells to which the magnetic bead 22 is not coupled are moved downwardly in the droplet type cell suspension by gravitation, thereby performing separation of the specific cells in the droplet type cell suspension.

After that, as cell buffer is supplied to the droplet type cell suspension via the cell suspension inlet 2, the droplet type cell suspension except the specific cells falls onto the droplet type cell suspension protecting part 6. The cell suspension sample that fell onto the droplet type cell suspension protecting part 6 is injected via the outlet 5, while the specific cells are picked and used for original purposes.

Figure 3:
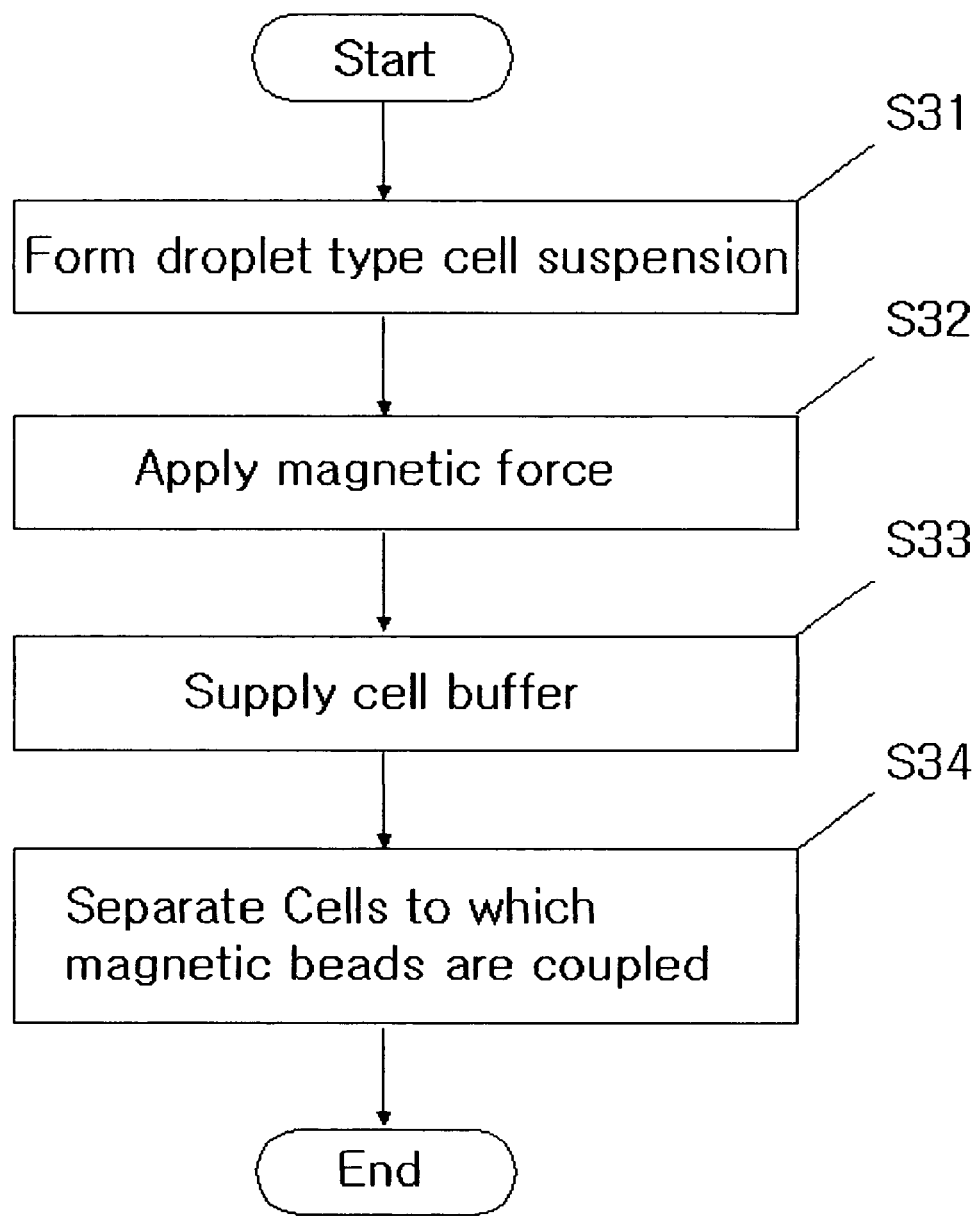
FIG. 3 illustrates a method of separating cells using magnets and droplet type cell suspension according to a preferred embodiment of the present invention.

FIG. 3 illustrates a method of separating cells using magnets and droplet type cell suspension according to a preferred embodiment of the present invention.

The method of separating cells includes forming droplet type cell suspension (S31), applying magnetic force to the formed droplet type cell suspension (S32), supplying the droplet type cell suspension with cell buffer (S33), and separating the specific cells (i.e. cells to which magnetic beads are coupled) from the droplet type cell suspension (S34).

To form droplet type cell suspension (S31) is to supply a droplet type cell suspension forming part with cell suspension sample through cell suspension inlet, thereby forming droplet type cell suspension having a certain size (e.g. diameter of 7 millimeters). The size of droplet type cell suspension may be regulated.

Then, magnetic force is applied to the formed droplet type cell suspension (S32), so that the specific cells moves in the droplet type cell suspension in a certain direction (e.g. towards the droplet type cell suspension forming part). Of course, intensity of the magnetic force applied to the specific cells contained the droplet type cell suspension is stronger than gravitation applied to the specific cells contained the droplet type cell suspension.

As cell buffer is further supplied to the droplet type cell suspension through the cell suspension inlet after magnetic force is applied, volume and weight of the droplet type cell suspension increases. Then, droplet type cell suspension except the specific cells, which moved towards the droplet type cell suspension forming part, falls onto the droplet type cell suspension protecting part.

Then, the specific cells are separated and used (S34). The specific cells may be picked after turning over the droplet type cell suspension forming part, while the magnet is positioned as it is. On the other hand, the specific cells may be picked after turning over the droplet type cell suspension forming part and removing the magnet.

Figure 4:
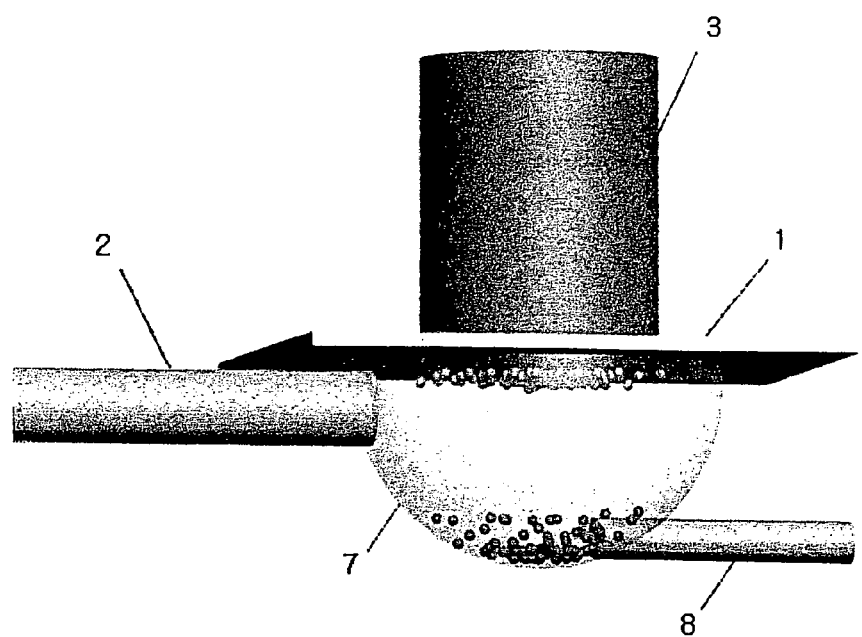
FIG. 4 illustrates that cells are separated by an apparatus of separating cells according to a preferred embodiment of the present invention.

FIG. 4 illustrates that cells are separated by an apparatus of separating cells according to a preferred embodiment of the present invention. FIG. 4 illustrates that the specific cells are completely separated from the other cells in the droplet type cell suspension.

As described above, according to the methods and apparatuses of separating cells using magnets and droplet type cell suspension, it is possible to reduce absorption problems because there is no need to use extra channel and metal balls. Further, it is possible to use the apparatus without regulating size thereof according to cells to be separated, to separate cells in case that amount of cell suspension is little as micro liter and to reduce size of whole apparatus due to small size of the droplet type cell suspension.

According to the methods and apparatuses, separation occurs in a chamber so that it is possible to reduce loss due to evaporation of cell buffer and to process much cell suspension sample in a short time.

The foregoing embodiments are merely exemplary and are not to be construed as limiting the present invention. Many alternatives, modifications and variations will be apparent to those skilled in the art.

The invention claimed is:

1. An apparatus for separating cells using magnets and droplet type cell suspension, comprising:
    a droplet type cell suspension forming part for forming a droplet type cell suspension under a lower part of the droplet type cell suspension forming part with cell suspension sample containing cells to which magnetic beads are coupled and wherein a region in which the droplet type cell suspension is to be formed, has a droplet type cell suspension forming part having a hydrophilic property and another region of the droplet type cell suspension forming part has a hydrophobic property;

a cell suspension inlet for supplying the droplet type cell suspension forming part with the cell suspension sample;

a magnet for applying magnetic force to the droplet type cell suspension;

a cell buffer inlet for supplying the droplet type cell suspension with cell buffer; and a temperature maintaining part for maintaining the temperature of the droplet type cell suspension.

2. The apparatus according to claim 1, further comprising:

an outlet for discharging cell buffer and cell suspension sample left after the cells to which magnetic beads are coupled are separated; and a droplet type cell suspension protecting part, connected to the outlet and spaced apart from the droplet type cell suspension forming part by a predetermined distance, for protecting the droplet type cell suspension.

3. The apparatus according to claim 2, wherein the droplet type cell suspension forming part regulates a size of droplet type cell suspension to be formed.

4. The apparatus according to claim 2, wherein the magnet applies attraction force to the cells to which the magnetic beads are coupled in the droplet type cell suspension.

5. The apparatus according to claim 2, wherein the magnet is not fixedly connected to the droplet type cell suspension forming part and is able to be easily separated from the droplet type cell suspension forming part.

6. The apparatus according to claim 2, wherein the temperature maintaining part maintains temperatures of the droplet type cell suspension and the droplet type cell suspension protecting part.

7. The apparatus according to claim 2, wherein the temperature maintaining part performs a cooling and a keeping warm simultaneously.

8. The apparatus according to claim 2, wherein the temperature maintaining part is implemented by a peltier element.

9. The apparatus according to claim 2, wherein the droplet type cell suspension protecting part prevents the droplet type cell suspension from evaporating.

10. The apparatus according to claim 2, wherein the droplet type cell suspension is formed under a lower part of the droplet type cell suspension forming part.

11. The apparatus according to claim 2, wherein the cell buffer inlet regulates vertical location of the cell buffer inlet itself.

12. An apparatus for separating cells using magnets and droplet type cell suspension, comprising:

a droplet type cell suspension forming part for forming a droplet type cell suspension under a lower part of the droplet type cell suspension forming part with cell suspension sample containing cells to which magnetic beads are coupled and wherein a region in which the droplet type cell suspension is to be formed, has a droplet type cell suspension forming part having a hydrophilic property and another region of the droplet type cell suspension forming part has a hydrophobic property:

a cell suspension inlet for supplying the droplet type cell suspension forming part with the cell suspension sample;

a magnet for applying magnetic force to the droplet type cell suspension;

a cell buffer inlet for supplying the droplet type cell suspension with cell buffer and regulating vertical location of the cell buffer inlet itself; and a droplet type cell suspension protecting part, connected to the outlet and spaced apart from the droplet type cell suspension forming part by a predetermined distance, for protecting the droplet type cell suspension.

13. The apparatus according to the claim 12, further comprising an outlet for discharging cell buffer and cell suspension sample left after the cells to which magnetic beads are coupled are separated.

* * * * *